(12) United States Patent
Gagnon

(10) Patent No.: US 7,999,085 B2
(45) Date of Patent: Aug. 16, 2011

(54) ENHANCED CAPACITY AND PURIFICATION OF PROTEIN BY MIXED MODE CHROMATOGRAPHY IN THE PRESENCE OF AQUEOUS-SOLUBLE NONIONIC ORGANIC POLYMERS

(75) Inventor: Peter S. Gagnon, San Clemente, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 12/422,141

(22) Filed: Apr. 10, 2009

(65) Prior Publication Data

US 2009/0247735 A1    Oct. 1, 2009

Related U.S. Application Data

(63) Continuation-in-part of application No. 11/970,296, filed on Jan. 7, 2008, now Pat. No. 7,691,980.

(60) Provisional application No. 60/879,484, filed on Jan. 9, 2007, provisional application No. 60/905,696, filed on Mar. 8, 2007, provisional application No. 60/913,162, filed on Apr. 20, 2007.

(51) Int. Cl.
*C07K 1/22* (2006.01)

(52) U.S. Cl. ..................................... 530/415

(58) Field of Classification Search ............ None
See application file for complete search history.

(56) References Cited

U.S. PATENT DOCUMENTS

| | | | | |
|---|---|---|---|---|
| 2,710,293 | A * | 6/1955 | Gerlough | 530/380 |
| 4,470,969 | A * | 9/1984 | Pancham et al. | 530/381 |
| 5,945,520 | A | 8/1999 | Burton et al. | |
| 6,498,236 | B1 | 12/2002 | Lihme et al. | |
| 6,870,034 | B2 | 3/2005 | Breece et al. | |
| 6,919,436 | B2 | 7/2005 | Lihme et al. | |
| 7,008,542 | B2 | 3/2006 | Belew et al. | |
| 7,385,040 | B2 | 6/2008 | Johansson et al. | |
| 7,691,980 | B2 * | 4/2010 | Gagnon | 530/390.1 |
| 2005/0107594 | A1 | 5/2005 | Sun et al. | |
| 2007/0259453 | A1 | 11/2007 | Engstrand et al. | |

OTHER PUBLICATIONS

Gagnon, Pete; "Purification Tools for Monoclonal Antibodies"; 1996, Validated Biosystems, Chapters 4-6, pp. 57-126.*
Gagnon, Pete et al.; "Nonionic Polymer Enhancement of Aggregate Removal in Ion Exchange and Hydroxyapatite Chromatography"; 2007, 12th Annual Waterside Conference, 33 pages.*
Gagnon, Pete et al.; "Method for obtaining unique selectivities in ion-exchange chromatography by addition of organic polymers to the mobile phase"; 1996, *Journal of Chromatography*, vol. 743, pp. 51-55.
Gagnon, Pete et al.; "Simultaneous removal of aggregates, leached protein A, endotoxin, and DNA from protein A purified IgG with CHT™ ceramic hydroxyapatite and CFT™ ceramic fluorapatite"; 2005, *Purification of Biological Products*, Santa Monica, 19 pages.
Gagnon, Pete et al.; "Obtaining Unique Selectivities in Ion Exchange Chromatography by Addition of Organic Polymers to the Mobile Phase"; 1995, *15th International Symposium on HPLC of Proteins, Peptides, and Polynucleotides*, 4 pages.
Gagnon, Pete et al.; "Improved antibody aggregate removal by hydroxyapatite chromatography in the removal of polyethylene glycol", 2008, *Journal of Immunological Methods*, vol. 336, No. 2, pp. 222-228.
Gagnon, Pete et al.; "A Non-Affinity Based Method for Purification of IgG Monoclonal Antibodies"; 2006, *IBC World Conference and Exposition*, 1 page.
"Macro-Prep Chromatography Supports"; Bio-Rad, 8 pages.
Ng, Paul K. et al; "Mechanistic model for adsorption of immunoglobulin on hydroxyapatite", 2006, *Journal of Chromatography A*, vol. 1142, No. 1, pp. 13-18.

* cited by examiner

*Primary Examiner* — David A Saunders
(74) *Attorney, Agent, or Firm* — Kilpatrick, Townsend & Stockton LLP

(57) ABSTRACT

This invention relates to the use of mixed mode chromatography for purification of a protein from a mixture containing other materials, including fragmented or aggregated antibodies, host cell proteins, DNA, endotoxin, and/or virus. This invention further relates to the integration of such a method into a multi-step procedure with other fractionation methods for purification of antibodies or other proteins suitable for in vivo applications.

17 Claims, 5 Drawing Sheets

ENHANCED CAPACITY AND PURIFICATION OF PROTEIN BY MIXED MODE CHROMATOGRAPHY IN THE PRESENCE OF AQUEOUS-SOLUBLE NONIONIC ORGANIC POLYMERS

CROSS-REFERENCE TO RELATED PATENT APPLICATIONS

This application is a continuation-in-part of U.S. patent application Ser. No. 11/970,296, filed Jan. 7, 2009 now U.S. Pat. No. 7,691,980, issued Apr. 6, 2010, which claims benefit of priority to each of U.S. Provisional Patent Application No. 60/879,484, filed Jan. 9, 2007; U.S. Provisional Patent Application No. 60/905,696, filed Mar. 8, 2007; and U.S. Provisional Patent Application No. 60/913,162, filed Apr. 20, 2007, each of which is incorporated by reference.

FIELD OF THE INVENTION

This invention relates to methods for enhancing purification of proteins by mixed mode chromatography. In certain embodiments, the enhancement may permit the chromatography method to bind greater amounts of protein or virus, thereby improving productivity and facilitating its practical use for initial capture of protein from unpurified preparations. In other embodiments, the enhancement may permit more effective separation of protein from other material (including, but not limited to, other proteins, DNA, endotoxin, or virus) and other contaminants. In other embodiments, the enhancement may permit more effective separation of non-aggregated antibody from aggregated antibody.

BACKGROUND OF THE INVENTION

Mixed mode chromatography involves the use of solid phase chromatographic supports that employ multiple chemical mechanisms to adsorb proteins or other solutes. Examples include but are not limited to chromatographic supports that exploit combinations of two or more of the following mechanisms: anion exchange, cation exchange, hydrophobic interaction, hydrophilic interaction, hydrogen bonding, pi-pi bonding, and metal affinity.

Mixed mode chromatography supports provide unique selectivities that cannot be reproduced by single mode chromatography methods such as ion exchange, however method development is complicated, unpredictable, and may require extensive resources. Even then, development of useful procedures may require long periods of time, as exemplified by hydroxyapatite.

Hydroxyapatite is a crystalline mineral of calcium phosphate with a structural formula of $Ca_{10}(PO_4)_6(OH)_2$. Chemically reactive sites include pairs of positively charged calcium atoms and triplets of negatively charged phosphate groups. The interactions between hydroxyapatite and proteins are multi-modal, hence its classification as a mixed mode support. One mode of interaction involves metal affinity of protein carboxyl clusters for crystal calcium atoms. Another mode of interaction involves cation exchange of positively charged protein amino residues with negatively charged crystal phosphates (Gorbunoff, *Analytical Biochemistry* 136 425 (1984); Kawasaki, J., *Chromatography* 152 361 (1985)).

The individual contributions of the two mechanisms to the binding and elution of a particular protein can be controlled in part by the choice of salts used for elution. The cation exchange interaction can be controlled with a gradient of any salt, including phosphate salts, sulfates, nitrates, or chlorides, specifically including sodium chloride and potassium chloride. The calcium affinity mode is inert to most commonly used non-phosphate salts. Thus proteins that bind by interaction with the calcium groups on hydroxyapatite cannot be eluted by sodium chloride alone. They can be eluted with phosphate salts.

Hydroxyapatite is commonly used for purification of antibodies, especially from partially purified preparations. The column is usually equilibrated and the sample applied in a buffer that contains a low concentration of phosphate. Adsorbed antibodies are often eluted in an increasing gradient of phosphate salts (Gagnon, Purification Tools for Monoclonal Antibodies, Chapter 5, *Validated Biosystems*, Tucson, ISBN 0-9653515-9-9 (1996); Luellau et al., *Chromatography* 796-165 (1998)). Gradients of phosphate combined with non-phosphate salts such as sodium chloride have also been used for protein purification, including antibody purification (Freitag, "Purification of a recombinant therapeutic antibody by hydroxyapatite chromatography," Oral presentation, 2d International Hydroxyapatite Conference, San Francisco (2001)). One such approach involves the application of a gradient of sodium chloride or potassium chloride while a low level of phosphate is held constant (Kawasaki et al., *Eur. J. Biochem.*, 155-249 (1986); Sun, "Removal of high molecular weight aggregates from an antibody preparation using ceramic hydroxyapatite," Oral presentation, 3rd International Hydroxyapatite Conference, Lisbon (2003); Gagnon et al., "Practical issues in the use of hydroxyapatite for industrial applications," Poster BIOT 322, 232nd meeting of the American Chemical Society, San Francisco, (2006) [http://www.validated.com/revalbio/pdffiles/ACS_CHT 0_02.pdf]; Wyeth et al., U.S. Patent Application, Publication No. WO/2005/044856 (2005)). This approach has also been applied to antibody purification with fluorapatite (Gagnon et al., "Simultaneous removal of aggregate, leached protein A, endotoxin, and DNA from protein A purified monoclonal IgG with ceramic hydroxyapatite and ceramic fluorapatite," Oral Presentation, Wilbio Conference on Purification of Biological Products, Santa Monica, (2005) [http://www.validated.com/revalbio/pdffiles/PBP_2005.pdf]). Fluorapatite is prepared by fluoridating hydroxyapatite. This substitutes fluoride for the hydroxyl groups creating a mineral with the structural formula $Ca_{10}(PO_4)_6F_2$.

Hydroxyapatite has been shown to yield a high degree of purification in a single step. However, the presence of phosphate and other ions may reduce binding capacity to a degree that makes either hydroxyapatite or fluorapatite economically unsuitable as capture methods (Gagnon et al., Hydroxyapatite as a Capture Method for Purification of Monoclonal Antibodies, IBC World Conference and Exposition, San Francisco (2006) [http://www.validated.com/revalbio/pdffiles/Gagnon_IBCSF06.pdf]). This prevents them from being competitive with capture methods that are relatively unaffected by phosphate and salt concentration, such as protein A affinity chromatography.

Most non-antibody protein contaminants elute before antibodies, but antibodies from different clones elute in different areas of the elution profile and may therefore overlap to varying degrees with contaminating proteins. Known methods for enhancing the separation are often ineffective and may be undesirable for economic reasons as well. For example, a shallow linear elution gradient can be applied but this has the negative side effects of increasing the buffer volume and process time, and it may still fail to achieve the desired purity.

Hydroxyapatite has been shown to be effective for removal of degraded forms of antibodies such as fragments, but selectivity is highly dependent on whether elution is conducted with a chloride gradient or with a phosphate gradient.

Hydroxyapatite and fluoroapatite have been shown to be effective for removal of aggregates from many antibody preparations. Antibody aggregates usually elute after antibodies but may coelute with antibodies to varying degrees. Aggregate removal is important because aggregates are known to contribute to nonspecific interactions that reduce the shelf stability, sensitivity, accuracy, and reproducibility of analytical results in conjunction with in vitro diagnostic applications. Aggregates are known to mediate adverse pharmacological effects, such as complement activation, anaphylaxis, or formation of therapy-neutralizing antibodies in conjunction with in vivo therapeutic applications. Aggregates also reduce purification efficiency by requiring additional steps to achieve adequately low aggregate levels in the final product. Elution of hydroxyapatite and fluorapatite with chloride gradients at low fixed concentrations of phosphate has been shown to be more effective than simple phosphate gradients, but even this approach may not be sufficient for all antibody preparations.

Various other mixed mode chromatography methods for antibody purification have been introduced in recent years. Examples of commercial products exploiting mixed mode functionalities include but are not limited to MEP Hypercel (Pall Corporation); Capto-MMC, Capto-Adhere, Capto-Q, Capto-S (GE Healthcare); and ABx (J.T. Baker). These products have varying degrees of ability to remove aggregates, host cell proteins, DNA, and virus from antibody preparations, but as with hydroxyapatite, method development is complex and unpredictable, and their utility as capture methods is often limited by low capacity.

Aqueous-soluble nonionic organic polymers are known in the field of protein purification for their ability to precipitate proteins, including antibodies. They have also been reported to increase the retention of proteins in protein A affinity chromatography and ion exchange chromatography (Gagnon, *Purification Tools for Monoclonal Antibodies*, Chapter 5, Validated Biosystems, Tucson, ISBN 0-9653515-9-9 (1996); Gagnon et al., "Multiple mechanisms for improving binding of IgG to protein A," Poster, BioEast, Washington D.C., (1992); Gagnon et al., "A method for obtaining unique selectivities in ion exchange chromatography by adding organic solvents to the mobile phase," Poster and Oral presentation, 15th International Symposium on HPLC of Proteins, Peptides, and Polynucleotides, Boston (1995) [http://www.validated.com/revalbio/pdffles/p3p95iec.pdf]). Such organic polymers include but are not limited to polyethylene glycol (PEG), polypropylene glycol, polyvinylpyrrolidone, dextran, cellulose, and starch, of various polymer molecular weights. PEG is an organic polymer with a structural formula of HO—$(CH_2$—$CH_2$—$O)_n$—H. In addition to its applications for protein fractionation, it is known as a protein stabilizer appropriate for use in pharmaceutical formulations.

SUMMARY OF THE INVENTION

The present invention relates to methods of purifying proteins (including but not limited to antibodies) from a preparation containing proteins to be purified by contacting said preparation with a mixed mode chromatography support in the presence of an aqueous-soluble (i.e., hydrophilic) nonionic organic polymer. Applicant surprisingly found that the presence of a nonionic organic polymer enhances binding capacity for virus or protein on mixed mode chromatography supports. In the case of protein capture this enables higher levels of productivity to be achieved, and expands the range of methods that may be considered for their initial capture from unpurified preparations. In the case of virus, this enables more effective viral clearance from the protein product Applicant further surprisingly found that the presence of nonionic organic polymer preferentially enhances the retention of antibody on mixed mode chromatography supports in comparison to most contaminating proteins, thereby enabling novel selectivity for improved removal of non-antibody proteins. Applicant further surprisingly found that the presence of nonionic organic polymer preferentially enhances retention of aggregated antibody and other very large molecules (e.g., viruses) on mixed mode chromatography supports in comparison to non-aggregated antibody, thereby enabling novel selectivity, superior separation, and superior removal capacity of large-contaminants including but not limited to virus. Most surprisingly, applicant found that the effects of soluble nonionic organic polymer on antibody binding and elution behavior are relatively uniform among different mixed mode chromatography methods, despite dramatic differences in their respective native selectivities. This is particularly valuable because it permits a uniform approach for applying the invention to any given antibody preparation, regardless of the composition of a particular mixed mode chromatography support.

The protein preparation may be applied to the mixed mode chromatography support in a variety of concentrations of nonionic organic polymer. In some embodiments, the concentration of nonionic organic polymer ranges from about 0.01% to 50%. In some embodiments, the concentration of nonionic organic polymer is between 0.1 to 50%, 1%-50%, 3%-50%, 5%-50%, 1%-70%, 1%-10%, 0.1%-10%, etc.

The concentration of nonionic organic polymer may be held constant or it may be altered throughout the course of the separation (including but not limited to in a gradient of increasing or decreasing concentration, or with step-wise changes in concentration).

The average molecular weight of the nonionic organic polymer can vary. In some embodiments, the average molecular weight ranges from, about 100 to 10,000 daltons, e.g., 100-1000, 1000-5000, etc.

In some embodiments, the nonionic organic polymer is PEG. In some embodiments, the PEG has an average molecular weight of 6,000 daltons and/or is applied at a concentration of 0.01 to 7.5%. In some embodiments, the PEG has an average molecular weight of 2,000 daltons and/or is applied at a concentration of 0.01 to 15%.

In some embodiments, a protein preparation is applied to the mixed mode chromatography support in the presence of nonionic organic polymer thereby resulting in increased protein- (including but not limited to, antibody-) binding and/or virus-binding capacity of the support. Thus, in some embodiments, a sufficient concentration of nonionic organic polymer is present in the relevant buffer to delay elution by 10% (or, e.g., 20%, 50%, etc.). For example, where an increasing gradient of a salt is used to elute the protein (e.g., antibodies), the center of the eluted antibody peak occurs at a concentration of the salt at least 10% higher than would occur in the absence of the nonionic organic polymer.

In some embodiments, a protein preparation is applied to the mixed mode chromatography support under conditions that permit the binding of virus or non-aggregated protein and contaminants, with fractionation of the virus or non-aggregated protein being achieved subsequently by changing the conditions such that the non-aggregated protein (e.g., antibody) is eluted while contaminants remain bound to the support. This mode of application is often referred to as "bind-elute" mode. In some embodiments, one or more proteins in the preparation is eluted and collected while virus remains bound to the support, thereby purifying the protein and reducing or eliminating viral contamination of the protein.

In some embodiments of bind-elute mode, the concentration of nonionic organic polymer is held constant during elution, while the pH is modified or the concentration of eluting salts is increased.

In some embodiments of bind-elute mode, the concentration of nonionic organic polymer is increased during elution, while the pH is modified or the concentration of eluting salts is increased.

In some embodiments of bind-elute mode, the concentration of nonionic organic polymers may be decreased during elution, while the pH and salt concentration are held constant.

The protein preparation may be applied to the mixed mode chromatography support under conditions that prevent the binding of non-aggregated protein while permitting the binding of aggregated protein and other large-molecules (including, e.g., viruses). This mode of application is often referred to as "flow-though" mode. Bound virus or aggregates of large molecules may be eluted subsequently upon treatment with an appropriate buffer.

Additional objects and advantages of the invention will be set forth in part in the description which follows, and in part will be obvious from the description, or may be learned by practice of the invention. The objects and advantages of the invention will be realized and attained by means of the elements and combinations specified in the claims.

The invention may be practiced in combination with one or more other methods, including but not limited to protein A and other forms of affinity chromatography, anion exchange chromatography, cation exchange chromatography, hydrophobic interaction chromatography, other mixed mode chromatography, and non-chromatographic methods. It is within the ability of a person of ordinary skill in the art to develop appropriate conditions for these methods and integrate them with the invention described herein to achieve purification of a particular antibody.

It is to be understood that both the foregoing general description and the following detailed description are exemplary and explanatory only and are not restrictive of the invention, as claimed.

The accompanying drawings, which are incorporated in and constitute part of this specification, and together with the description, serve to explain the principles of the invention.

DETAILED DESCRIPTION OF THE INVENTION

A. Definitions

Figure 1:
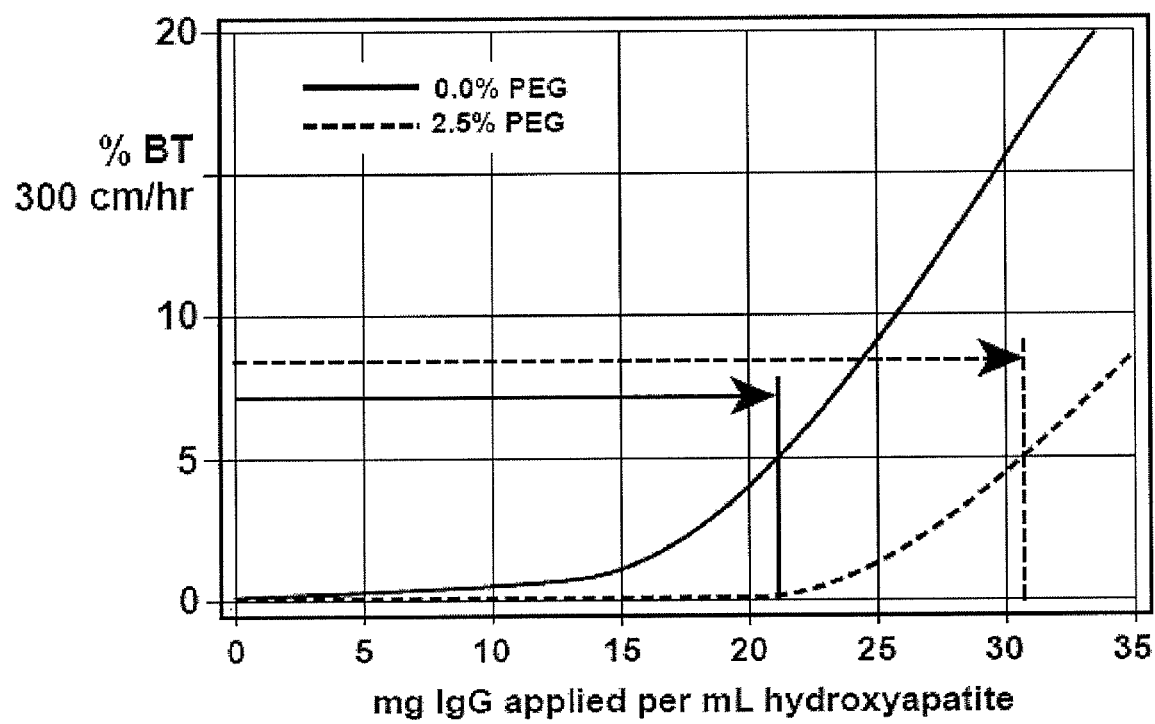
FIG. 1 illustrates an application of the invention in which nonionic organic polymer is used to increase dynamic binding capacity of an antibody preparation on hydroxyapatite.

Terms are defined so that the invention may be understood more readily. Additional definitions are set forth throughout the detailed description.

"Single mode support" refers to a chromatographic solid phase that involves substantially a single chemical adsorption mechanism. Examples include cation exchangers and anion exchangers.

"Mixed mode chromatography support" refers to a chromatographic solid phase that substantially involves a combination of two or more chemical mechanisms. In some embodiments, the combination results in unique selectivities such that it is able to achieve fractionation among antibodies, antibody aggregates, antibody fragments, other proteins, DNA, endotoxin, and virus, that cannot be achieved by a single mode support. Examples of chemical mechanisms that can be combined in mixed mode supports include but are not limited to cation exchange, anion exchange, hydrophobic interaction, hydrophilic interaction, hydrogen bonding, pi-pi bonding, and metal affinity. The solid phase can be a porous particle, nonporous particle, membrane, or monolith.

"Nonionic organic polymer" refers to an aqueous-soluble uncharged linear or branched polymer of organic composition. Examples include, but are not limited to dextran, starch, cellulose, polyvinylpyrrolidone, polypropylene glycol, and polyethylene glycol of various molecular weights. Polyethylene glycol has a structural formula $HO-(CH_2-CH_2-O)_n-H$. Examples include, but are not limited to compositions with an average polymer molecular weight ranging from 100 to 10,000 daltons. The average molecular weight of commercial PEG preparations is typically indicated by a hyphenated suffix. For example, PEG-6000 refers to a preparation with an average molecular weight of about 6,000 daltons.

"Antibody" refers to an immunoglobulin, composite, or fragmentary form thereof. The term may include but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibody" may also include composite forms including but not limited to fusion proteins containing an immunoglobulin moiety. "Antibody" may also include antibody fragments such as Fab, F(ab')2, Fv, scFv, Fd, dAb, Fc and other compositions, whether or not they retain antigen-binding function.

"Protein preparation" refers to any composition containing a protein to be purified. In some cases, the protein to be purified is an antibody. "Antibody preparation" refers to any composition containing a non-aggregated antibody. Said preparation may also contain antibody fragments and/or aggregates. Non-antibody proteins and other contaminants, potentially including but not limited to nucleic acids, endotoxin, and virus may also be present.

"Aggregate" refers to an association of at least two antibodies and often more (e.g., 5, 10, 20 or more antibodies). The association may be either covalent or non-covalent without respect to the mechanism by which the antibodies are associated. The association may be direct between the antibodies or indirect through other molecules that link the antibodies together. Examples of the latter include but are not limited to disulfide linkages via other proteins, hydrophobic associations via lipids, charge associations via DNA, affinity associations via leached protein A, or mixed mode associations via multiple components.

"Complex" refers to an association of an antibody with one or more non-antibody molecules. The association may be either covalent or non-covalent without respect to the mechanism of association. Examples include but are not limited to associations with other proteins, lipids, DNA, leached protein A, or multiple components.

"Bind-elute mode" as it relates to the invention herein, refers to an operational approach to chromatography in which the buffer conditions are established so that both a target protein (e.g., non-aggregated antibody) and undesired contaminants bind to the mixed mode chromatography support when the protein preparation is applied in the presence of nonionic organic polymer. Fractionation of intact non-aggregated protein is achieved subsequently by changing the conditions such that the target of interest is eluted from the support while contaminants remain bound. These contaminants may optionally be removed by an appropriate cleaning buffer.

"Flow-through mode" as it relates to the invention herein, refers to an operational approach to chromatography in which the buffer conditions are established so that intact non-aggregated protein to be purified flows through the mixed mode chromatography support upon application, while aggregates and other large molecules (including viruses) are selectively retained, thus achieving their removal.

"Preparative applications" refers to situations in which the invention is practiced for the purpose of obtaining purified protein for research, diagnostic, therapeutic, or other applications. Such applications may be practiced at any scale, ranging from milligrams to kilograms of antibody per batch.

"In-line dilution" refers to a method of chromatographic sample equilibration that can be used to avoid antibody precipitation before it can bind to the column. Advance addition of nonionic organic polymer to an antibody preparation may cause antibody to precipitate over a period of time. Such precipitates may cause problems if applied to a packed chromatography column. In-line dilution adds nonionic organic polymer to the antibody preparation as it is being pumped onto the column. Conditions may be used under which pre-column contact time of antibody (or other target) to nonionic organic polymer is too brief for antibody (or other target) precipitation to occur.

B. Materials

1. Mixed Mode Chromatography Supports

Various mixed mode chromatography media are available commercially, any of which can be used to practice of this invention. Commercially available examples include but are not limited to ceramic hydroxyapatite (CHT) or ceramic fluorapatite (CFT), MEP-Hypercel™, Capto-MMC™, Capto-Adhere™, Capto-S™, Capto-Q™, and ABx™.

"Hydroxyapatite" refers to a mixed mode support comprising an insoluble hydroxylated mineral of calcium phosphate with the structural formula $Ca_{10}(PO_4)_6(OH)_2$. Its dominant modes of interaction are phosphoryl cation exchange and calcium metal affinity.

"Fluorapatite" refers to a mixed mode support comprising an insoluble fluoridated mineral of calcium phosphate with the structural formula $Ca_{10}(PO_4)_6F_2$. Its dominant modes of interaction are phosphoryl cation exchange and calcium metal affinity.

"Ceramic" hydroxyapatite (CHT) or "ceramic" fluorapatite (CFT) refer to forms of the respective minerals in which nanocrystals are agglomerated into particles and fused at high temperature to create stable ceramic microspheres suitable for chromatography applications. Commercial examples of ceramic hydroxyapatite include, but are not limited to CHT Type I and CHT Type II. Commercial examples of fluorapatite include, but are not limited to CFT Type I and CFT Type II. Unless specified, CHT and CFT refer to roughly spherical particles of any average diameter, including but not limited to about 10, 20, 40, and 80 microns. The choice of hydroxyapatite or fluorapatite, the type, and average particle diameter can be determined by the skilled artisan.

In some embodiments, the mixed-mode chromatography support exploits a combination of anion exchange and hydrophobic interaction functionalities. Examples of such supports include, but are not limited to, MEP-Hypercel™.

In some embodiments, the mixed-mode chromatography support exploits a combination of cation exchange and hydrophilic interaction functionalities. Examples of such supports include, but are not limited to, Capto-S™.

In some embodiments, the mixed-mode chromatography support exploits a combination anion exchange and hydrophilic interaction functionalities. Examples of such supports include, but are not limited to, Capto-Q™.

In some embodiments, the mixed-mode chromatography support exploits a combination of cation exchange, anion exchange, and hydrophobic interaction functionalities. Examples of such supports include, but are not limited to, ABx™.

In some embodiments, the mixed-mode chromatography support exploits a combination of anion exchange and hydrophobic interaction functionalities with potential for hydrogen bonding and pi-pi bonding. Examples of such supports include, but are not limited to, Capto-Adhere™.

In some embodiments, the mixed-mode chromatography support exploits a combination of cation exchange and hydrophobic interaction functionalities with potential for hydrogen bonding and pi-pi bonding. Examples of such supports include, but are not limited to, Capto-MMC™.

The invention may be practiced in a packed bed column, a fluidized/expanded bed column containing the hydroxyapatite or fluorapatite, and/or a batch operation where the mixed mode support is mixed with the antibody preparation for a certain time.

In some embodiments, a mixed mode chromatography support is packed in a column.

In some embodiments, the mixed mode support is packed in a column of at least 5 mm internal diameter and a height of at least 25 mm. Such embodiments are useful, e.g., for evaluating the effects of various conditions on a particular antibody or other target protein.

Another embodiment employs the mixed mode support, packed in a column of any dimension required to support preparative applications. Column diameter may range from less than 1 cm to more than 1 meter, and column height may range from less than 1 cm to more than 30 cm depending on the requirements of a particular application.

It will be appreciated that the present invention is not limited to the above heights and diameters. Appropriate column dimensions can be determined by the skilled artisan.

2. Proteins

Protein (antibody or non-antibody protein) preparations to which the invention can be applied can include, but are not limited to, unpurified or partially purified proteins (including, e.g., antibodies) from natural, synthetic, or recombinant sources. Unpurified protein a preparations can come from various sources including, but not limited to, plasma, serum, ascites, milk, plant extracts, bacterial lysates, yeast lysates, or conditioned cell culture media. Partially purified preparations can come from unpurified preparations that have been processed by at least one chromatography, precipitation, other fractionation step, or any combination of the foregoing. The chromatography step or steps can employ any method, including but not limited to affinity, anion exchange, cation exchange, protein A affinity, hydrophobic interaction, immobilized metal affinity, or mixed-mode chromatography. The precipitation step or steps can include any method including, but not limited to, salt or PEG precipitation. Other fractionation steps can include, but are not limited to, crystallization or membrane filtration. The proteins (including but not limited to antibodies) can be PEGylated or alternatively, not PEGylated.

Exemplary non-antibody proteins include any protein with a therapeutic, industrial, diagnostic, or other effect. Such proteins can be naturally-occurring or recombinant. The proteins can be generated in tissue or cell cultures or isolated from animals or plants.

Proteins (e.g., antibodies or non-antibody proteins) can be purified in either flow-through mode or bind-elute mode, as described herein.

3. Nonionic Organic Polymers

Various commercially available nonionic organic polymers can be used to practice the invention. Examples include, but are not limited to polyethylene glycol (PEG), polypropylene glycol, cellulose, dextran, starch, and polyvinylpyrrolidone.

PEG provides a general model for behavior of soluble nonionic organic polymers within the context of the invention. Thus, while PEG is discussed in the following text, one should recognize that the information applies equally to other nonionic polymers, including but not limited to those specifically listed herein.

The invention may be practiced with PEG with an average polymer molecular weight ranging from about 100 to about 10,000 Daltons. Exemplary PEG includes PEG having an average molecular weight of, e.g., 200, 300, 400, 500, 900, 1000, 1400, 2000, 3300, 4500, 8000, 10000, 14000, etc. In some embodiments, the PEG has an average weight between 400-1000, 200-1000, 400-2000, or 1000-5000. A wide variety of different PEGs are available from, e.g., Aldrich.

PEG or other organic polymers can be linear or branched polymers.

Lower molecular weight PEGs will generally require a higher concentration to achieve an effect similar to higher molecular weight PEGs.

Lower concentrations of a given molecular weight of PEG are generally used to enhance the binding of larger proteins (e.g., larger antibodies and fusion proteins) as well as viruses compared to concentrations to the concentration of PEG to result in the same amount of enhanced binding of smaller proteins. For example, IgM, with an approximate molecular weight of about 960 kD, will generally require a lower concentration of PEG to achieve a certain degree of binding enhancement than IgG, with an approximate molecular weight of 160 kD. Retention of aggregates, complexes, and other large molecule contaminants will generally be enhanced to a greater degree than the unaggregated forms of the proteins from which they are derived.

Lower concentrations of PEG will be generally required to enhance the binding of molecules that are strongly retained by the mixed mode chromatography support, compared to the concentration for PEG to achieve the same enhanced binding for molecules that are weakly retained.

The effects described in the two preceding paragraphs will generally be compound: the retention of large molecules that are strongly retained in the absence of nonionic organic polymer will be enhanced more by application of the invention than molecules that are smaller and weakly retained, smaller and strongly retained, or larger and weakly retained.

In some embodiments, PEG with an average molecular weight of about 6,000 Daltons is employed in a concentration range from 0.0-7.5% to separate intact IgG from aggregated forms (see figures).

In some embodiments, PEG with an average molecular weight of about 2,000 Daltons is employed in a concentration range from 0.0-15.0% to separate intact IgG from aggregated forms.

The identity, appropriate average molecular weight, and concentration of the organic polymer to practice the invention can be determined by the skilled artisan.

C. Description of the Method

In preparation for contacting the protein (e.g., antibodies) preparation with the mixed mode support, in some embodiments, the chemical environment inside the column is equilibrated. This is commonly accomplished by flowing an equilibration buffer through the column to establish the appropriate pH; conductivity; identity, molecular weight, and concentration of nonionic organic polymer; and other pertinent variables.

In some embodiments, the protein (e.g., antibody) preparation is also equilibrated to conditions compatible with the column equilibration buffer before the invention can be practiced. This generally consists of adjusting the pH, salt concentration; the identity, average molecular weight and concentration of nonionic organic polymer.

In one embodiment, nonionic organic polymer is added to directly the protein (e.g., antibody) preparation before it is applied to the column. However this potentially limits the amount of nonionic organic polymer that can be used because an excessive concentration of polymer may cause the protein (e.g., antibody) or other components of the preparation to precipitate before the sample can be loaded on the column.

In another embodiment, nonionic organic polymer is added to the protein (e.g., antibody) preparation by means of in-line dilution. This allows a higher percentage of nonionic organic polymer to be employed, because the pre-column contact time of the polymer with the sample is reduced to seconds or less. Appropriate conditions can be determined by the skilled artisan.

In some embodiments, after the column and protein (e.g., antibody) preparation is equilibrated, the protein preparation may be contacted with the column. The protein preparation may be applied at a linear flow velocity in the range of, for example, about 50-300 cm/hr. Appropriate flow velocity can be determined by the skilled artisan.

In one embodiment of the flow-through mode, non-aggregated protein (e.g., antibody) flows through the column and is collected, while virus and/or aggregated protein binds to the column. Optionally, the protein preparation is followed with a wash buffer, usually of the same composition as the equilibration buffer. This displaces remaining non-aggregated protein from the column so that it can be collected. Retained aggregates may optionally be removed from the column with an appropriate cleaning buffer.

Flow-through mode conditions can be developed depending on the specific protein desired. Without intending to limit the scope of the invention, the following description is provided as a guide for developing flow-through conditions as desired for a particular protein. In some embodiments, a PEG (or other soluble nonionic organic polymer) concentration is identified whereby aggregates or other undesirable components of the preparation would bind to the mixed-mode column and non-aggregated protein would not. For example, phosphate, sodium chloride, other salts, or a combination thereof, can be tested at a variety of concentrations and conditions, initially in the absence of soluble nonionic organic polymer to identify conditions at which target and contaminant (e.g., antibody/antibody aggregate or protein/virus) elute. Increasing (or decreasing) amount of soluble nonionic organic polymer is then injected into the sample until the appropriate concentration is identified at which the target (e.g., non-aggregated antibody, non-antibody protein, etc.) flows through but the aggregate and/or other contaminant remains bound to the column.

In one embodiment of an application conducted in bind-elute mode, both aggregated and non-aggregated protein and/or virus bind to the column. In some embodiments, sample application is followed with a wash buffer, usually of the same composition as the equilibration buffer (optionally lacking, or having a reduced amount of, the soluble nonionic organic polymer). This removes unretained contaminants from the column. Non-aggregated protein is then eluted from the column under conditions that leave aggregated protein or other contaminants such as viruses bound to the column. Retained contaminants may optionally be removed from the column with an appropriate cleaning buffer.

In one embodiment of the bind-elute mode, the wash buffer may have a formulation different than the equilibration buffer.

The skilled artisan will recognize that various strategies of manipulating nonionic organic polymer concentration during elution will permit successful application of the invention.

In one embodiment of the bind-elute mode, the concentration of nonionic organic polymer is held constant during elution, while the pH is altered and/or the concentration of eluting salts is increased. For example, in some embodiments, the target (e.g., antibody or other protein) is eluted in, e.g., 0.1-0.8 M phosphate, or optionally, at relatively low concentrations of phosphate (e.g., less than 0.2 or less than 0.1 M) but with additional salts (e.g., NaCl, KCl, etc.), e.g., at 0.3 M or more, 0.5 M or more, etc.

In another embodiment of the bind-elute mode, the concentration of nonionic organic polymer is decreased during elution, while the pH and concentration of eluting salts is held constant.

In another embodiment of the bind-elute mode, the concentration of nonionic organic polymer is increased during elution, while the concentration of eluting salts is also increased. This embodiment will often give the best separation between non-aggregated and aggregated protein and/or virus because the later-eluting aggregates/virus experience a higher concentration of nonionic organic polymer, preferentially enhancing their retention and increasing their separation from non-aggregated protein.

After use, the mixed mode column may optionally be cleaned, sanitized, and stored in an appropriate agent, and optionally, re-used.

In some embodiments, the invention will have a beneficial effect on removal of other contaminants, including but not limited to, nucleic acids, endotoxin, virus, and complexes of antibody with leached protein A.

Exemplary viruses that can be removed by the methods of the invention include, e.g., membrane-encapsulated viruses as well as non-encapsulated viruses. Contaminating viruses may derive from the cell lines used to produce a given protein product, or from exogenous contamination. Viruses that can be removed by the methods of the invention may also include viruses that are deliberately introduced as markers for the purpose of quantifying and validating the ability of a given purification method to effectively remove the introduced virus. Exemplary viruses to be removed include but not limited to, HIV, HBV, HCV, and HPV, and non-human animal viruses, including but not limited to, minute virus of mouse (MVM), and murine leukemia virus (MuLV).

D. Additional Optional Steps

The present invention may be combined with other purification methods to achieve higher levels of purification. Examples include, but are not limited to, other methods commonly used for purification of proteins, such as affinity chromatography (e.g., such as protein A affinity chromatography for purification of antibodies), anion exchange chromatography, cation exchange chromatography, hydrophobic interaction chromatography, immobilized metal affinity chromatography, additional mixed mode chromatography methods, precipitation, and filtration.

Removal of residual organic polymer from purified protein, if desired, can be accomplished without need for a specific nonionic organic polymer removal step. In some embodiments, the nonionic organic polymer can be omitted from the wash and elution steps, so that the eluted antibody is substantially polymer-free. Alternatively, if the target protein is bound to a chromatography medium in a subsequent process step, residual nonionic organic polymer will pass through the column. This approach will work with most ion exchangers, mixed mode, and affinity methods. Removal of residual nonionic polymer can also be facilitated by employing polymers of low average molecular weight so that they can be removed by diafiltration or other buffer exchange methods.

EXAMPLES

It is well known in the art of antibody purification that considerable variation in chromatographic behavior is encountered from one antibody preparation to another. This includes variation in the composition and proportion of non-antibody proteins, antibody fragments, and aggregates that contaminate various antibody preparations, as well as variation in the individual retention characteristics of different antibodies. This makes it necessary to customize the buffer conditions to apply the invention to its best advantage in each situation. This may involve adjustment of pH, the concentration of salts, the concentration pH buffering components, choice of the identity, average molecular weight and concentration of nonionic organic polymer. Appropriate levels for the various parameters and components can be determined systematically by a variety of approaches. The following examples are offered for illustrative purposes only.

Example 1

Bind-elute mode, enhancement of binding capacity. See, FIG. 1. A column of hydroxyapatite, CHT Type II, 20 micron, 5 mm diameter, 50 mm height, is equilibrated at a linear flow rate of 300 cm/hr with 5 mM sodium phosphate at pH 6.7. A monoclonal antibody preparation IgG1, 1 mg/ml) previously purified by protein A affinity chromatography is equilibrated to the same conditions and applied to the column. The effluent is monitored for UV absorbance at 280 nm to characterize the binding capacity of the column. The column is then cleaned with about 600 mM potassium phosphate, pH 6.7. The run is repeated but with about 2.5% PEG-6000 added to the sample and column equilibration buffer. Different molecular weights or concentrations of PEG, and variations in other parameters, may be evaluated in subsequent iterations to determine the formulation that provides the best results for the particular antibody. Other nonionic organic polymers may be evaluated as well.

Example 2

Figure 2:
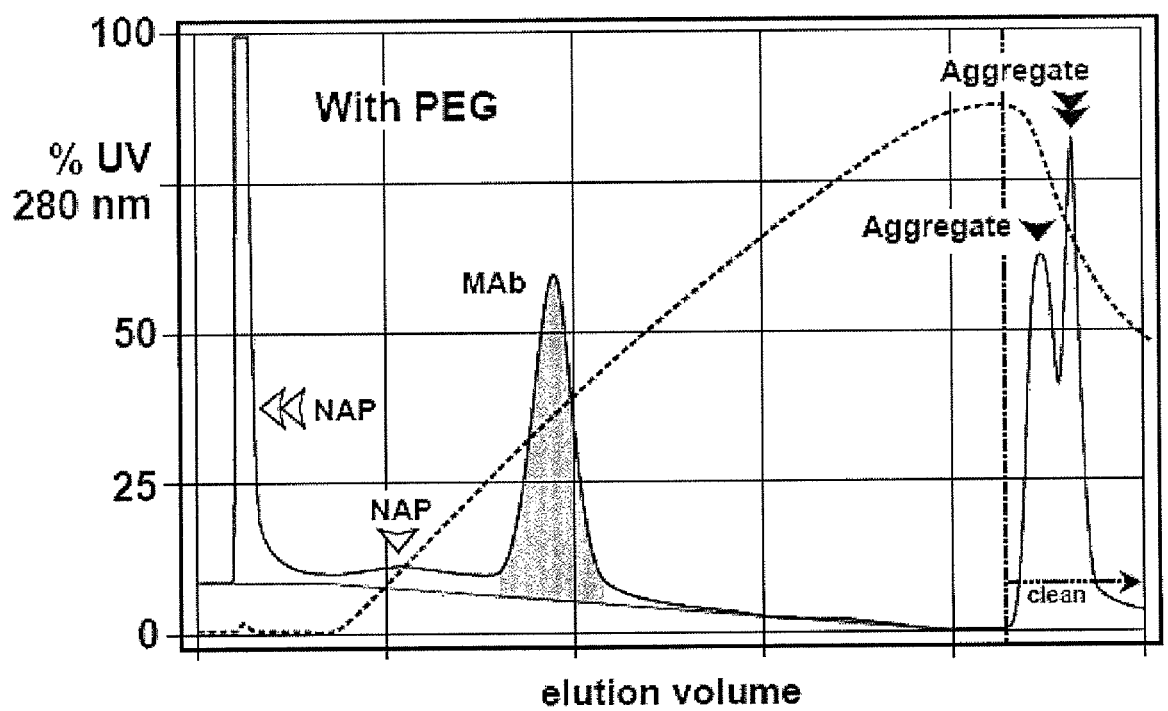
FIG. 2 illustrates an application of the invention in which nonionic organic polymer is used to improve removal of non-antibody protein ("NAP"), aggregated antibody, and other contaminants from an antibody preparation by hydroxyapatite chromatography.

Bind-elute mode, enhanced removal of non-antibody protein contaminants and aggregates from a preparation of unpurified monoclonal antibody. A column of hydroxyapatite, CHT Type II, 20 micron, 5 mm diameter, 5 cm height, is equilibrated at a linear flow rate of 300 cm/hr with 5 mM sodium phosphate at pH 6.7. An unpurified antibody preparation (unpurified chimeric IgG1) is applied to the column, washed with equilibration buffer, then eluted with a gradient to 5 mM sodium phosphate, 2.0 M sodium chloride, pH 6.7. The run is repeated but eluted with linear gradient to about 5 mM sodium phosphate, 2.0 M sodium chloride, and about 5% PEG-6000, and cleaned with 500 mM sodium phosphate at 300 cm/hr (1 ml/min) (see, FIG. 2). In a subsequent iteration, the run is repeated except that the concentration of PEG-6000 in the gradient endpoint buffer is increased to 3.75%. Different molecular weights or concentrations of PEG, and variations in other parameters, may be evaluated in subsequent iterations to determine the formulation that provides the best results for the particular antibody. Other nonionic organic polymers may be evaluated as well.

Example 3

Figure 3:
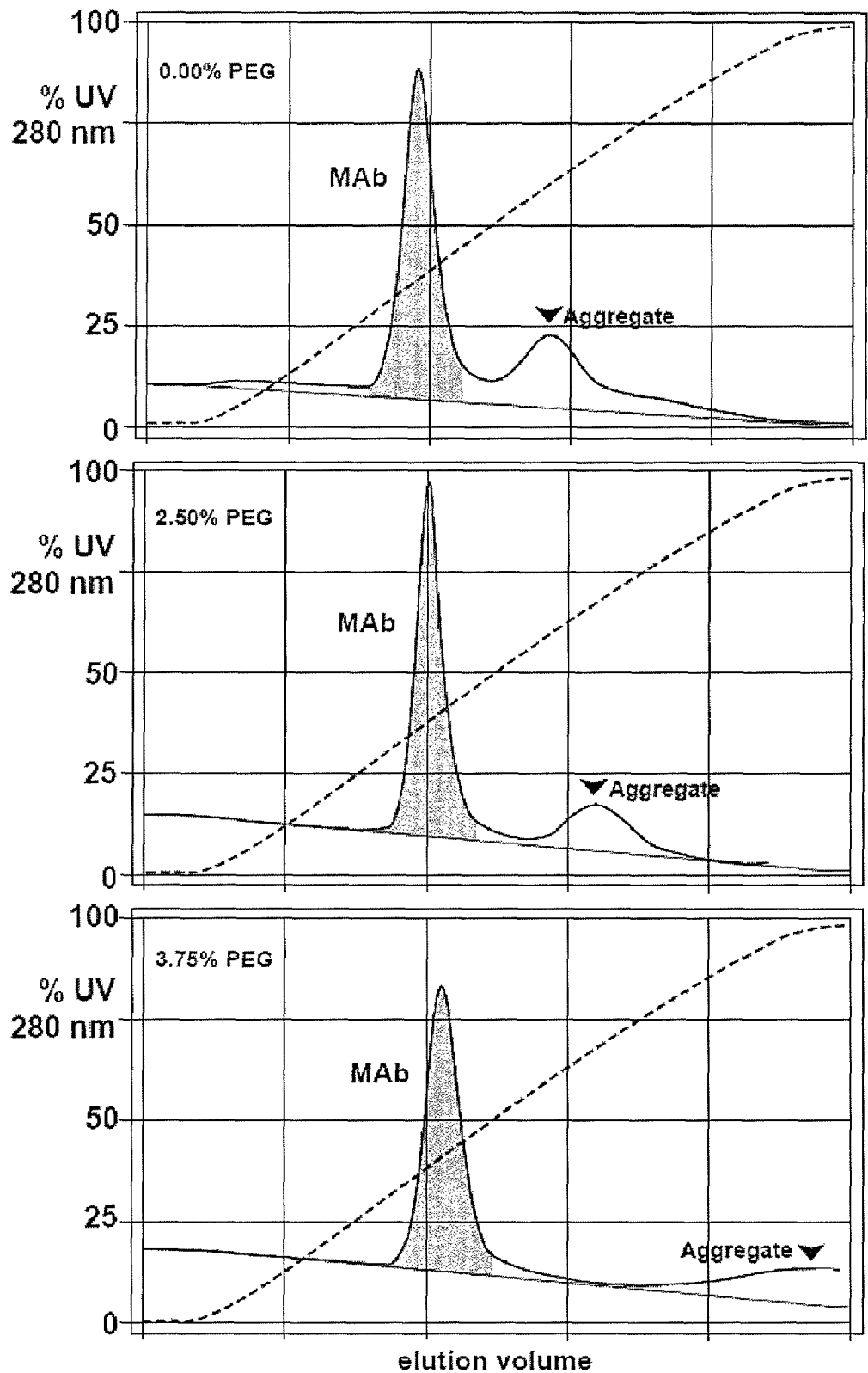
FIG. 3 illustrates an application of the invention in which nonionic organic polymer is used to improve the separation of aggregated and non-aggregated antibody from an antibody preparation by hydroxyapatite chromatography.

Bind elute mode, enhanced removal antibody aggregates from a preparation or protein A purified monoclonal antibody. See, FIG. 3. A column of hydroxyapatite, CHT Type I, 20 micron, 5 mm diameter, 5 cm height, is equilibrated at a linear flow rate of 300 cm/hr with 5 mM sodium phosphate at pH 6.7. The partially purified antibody preparation (human IgG1 purified by protein A affinity chromotography) is applied to the column, washed with equilibration buffer, then eluted with a linear gradient to 5 mM sodium phosphate, 2.0 M sodium chloride, pH 6.7 at a linear flow rate of 600 cm/hr (2 ml/min). The run is repeated but eluted with a gradient to about 5 mM sodium phosphate, 2.0 M sodium chloride, and up to 7.5% PEG-6000. Different molecular weights or concentrations of PEG, and variations in other parameters, may be evaluated in subsequent iterations to determine the formulation that provides the best results for the particular antibody. Other nonionic organic polymers may be evaluated as well.

Example 4

Figure 4:
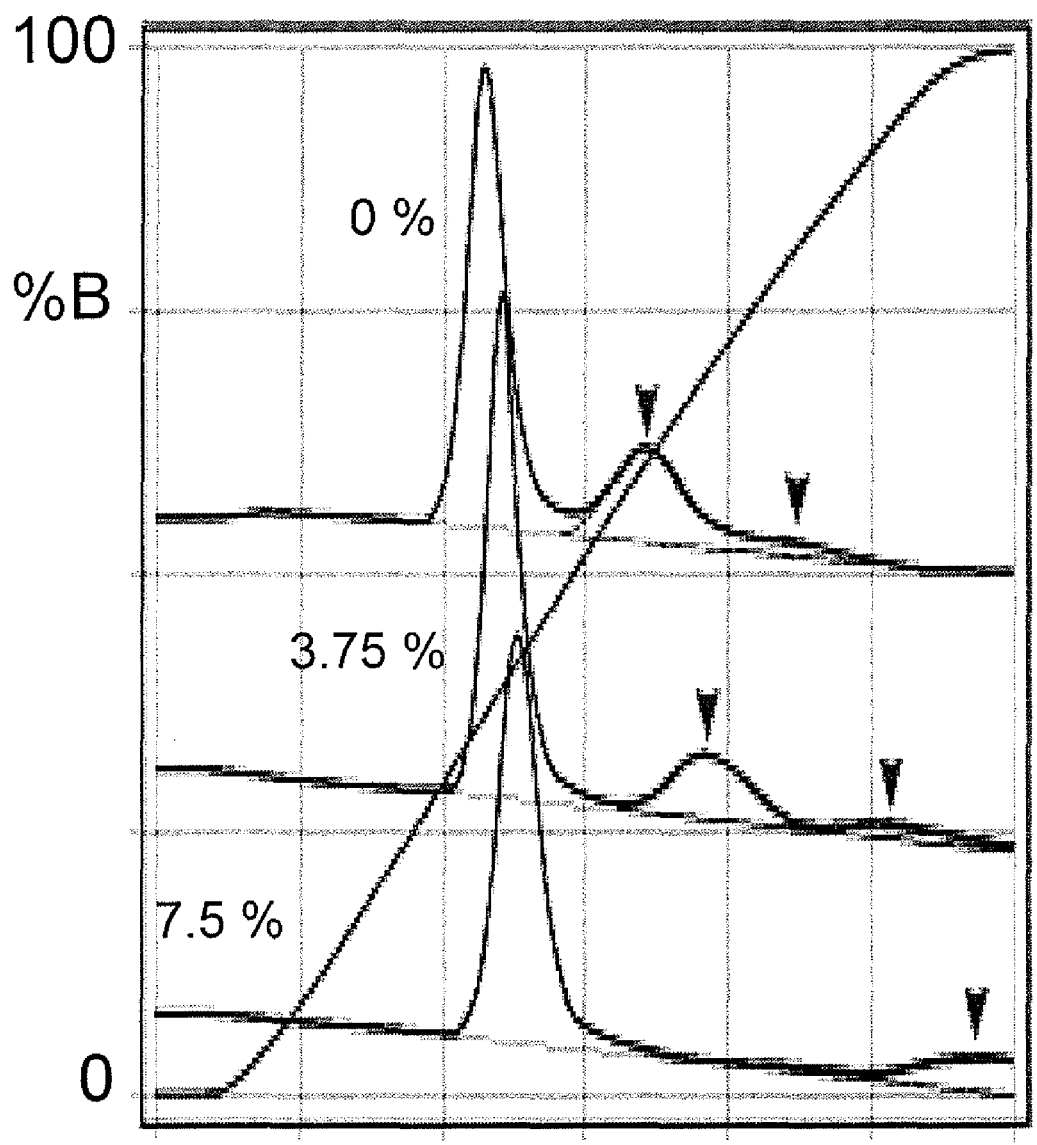
FIG. 4 illustrates an application of the invention in which nonionic organic polymer is used to improve the separation of aggregated antibody by hydroxyapatite chromatography. The arrows in the figure identify peaks of aggregated antibody.
Figure 5:
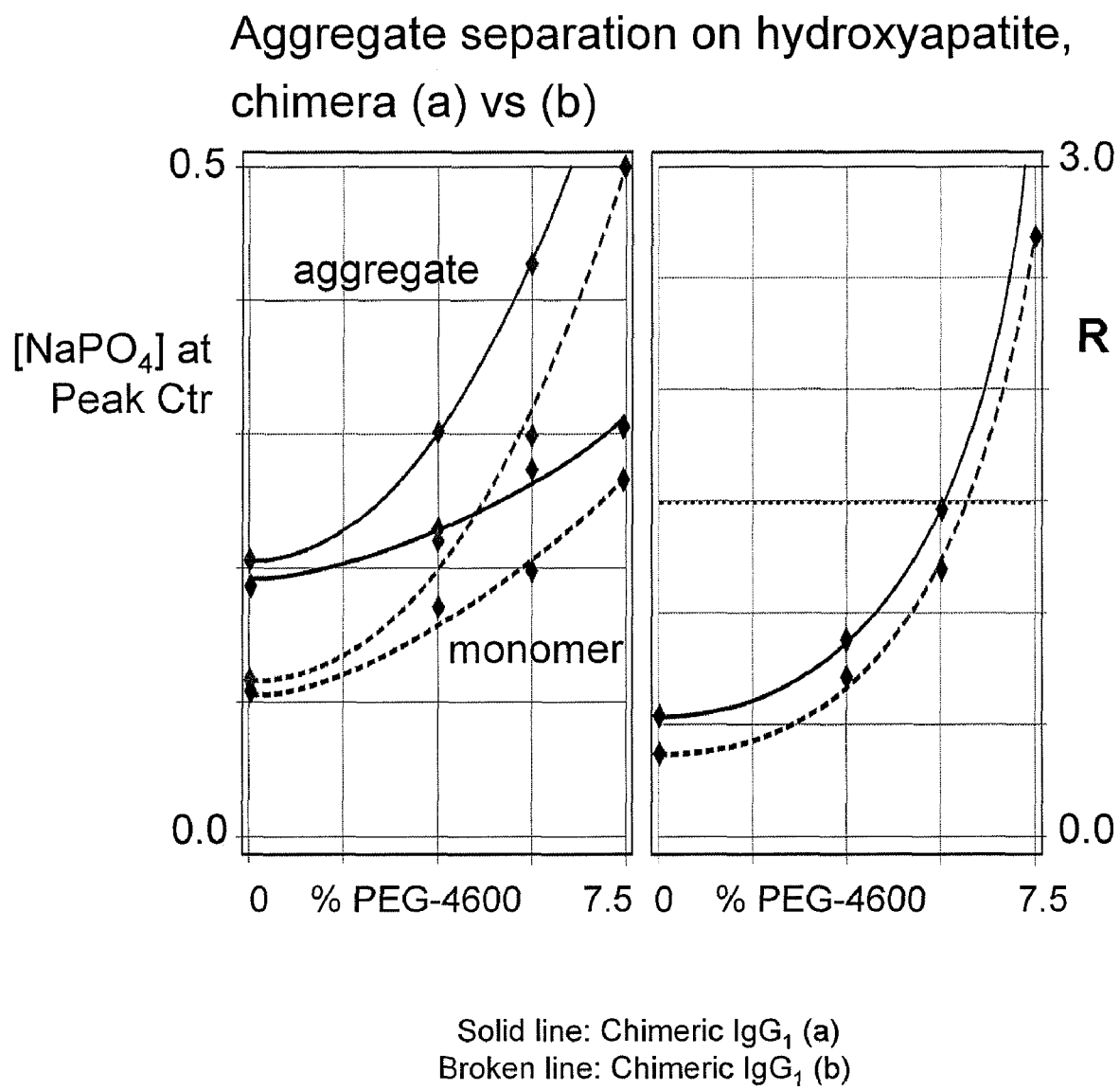
FIG. 5 illustrates separation of antibody aggregates from antibody monomers. The left graph shows that while each of two different antibodies ("chimera (a)" and "chimera (b)") had different elution characteristics, on hydroxyapatite, the addition of PEG affected them in nearly the same way. This demonstrates that the effect of PEG dominates the selectivity of the system. This in turn illustrates that the method is broadly applicable to different antibodies and results in separation of aggregates from monomers that does not occur in the absence of PEG. The right graph shows that the degree of separation of monomer and aggregate peaks is enhanced in the presence of even modest amounts of PEG. R values of 1.5 and over generally indicates a baseline between the peaks, meaning that one peak can be fully eluted before the second peak begins elution.

Bind elute mode, enhanced removal antibody aggregates from a preparation or protein A purified monoclonal antibody. See, FIG. 4. A column of hydroxyapatite, CHT Type I, 20 micron, 5 mm diameter, 5 cm height, is equilibrated at a linear flow rate of 300 cm/hr (1 ml/min) with 10 mM sodium phosphate at pH 7.0. The partially purified antibody preparation (chimeric IgG1(a)) is applied to the column, washed with equilibration buffer, then eluted with a linear gradient to 500 mM sodium phosphate, pH 7.0 within 20 column volume. The run is repeated once under the same conditions but with 3.75% PEG-6000, and a second time under the same conditions but with 7.5% PEG-6000.

Example 5

Viral clearance via hydroxyapatite chromatography has been studied for at least 45 years [Shukla, Abhinav A. et al., Journal of Chromatography, B, 848:28-39 (2006); Pfefferkorn, E. R., and Hunter, H. S., Virology, 20:433-445 (1963); Dove G B et al., Purification alternatives for IgM (human) monoclonal antibodies, p 194-209 in Ladisch M R, Builder S E, Painton, C C and Willson, R C (eds), ACS Symposium Series 427, American Chemical Society, Washington, D.C. (1998); Grun J B, White E M and Sito A F, Biopharm, 5:22-30 (1992)]. The mechanism of binding can be due to either synergistic effects of multi-site binding [Aoyama, K. and Chiba, J., J. Imm. Meth., 162:201-210 (1993); Luellau, E. et al., Journal of Chromatography, A, 796:165-175 (1998); Josic D. et al., Biol. Chem. Hoppe Seylar, 372(3):149-156 (1991)], strong interactions of clustered surface phosphates (in the case of lipid enveloped viruses) with calcium [Sleigh, R W et al., J Dairy Res., 46:337-42 (1979); Gagnon, P., BioProcess Int., 4(2):50-60 (2006)] or both. The original eluant used almost exclusively for hydroxyapatite was phosphate. However, sodium chloride as an eluant has also been used for some 50 years [Hjerten, S., Biochim. Biophys. Acta, 31:216-235 (1959)], with improvements noted for antibody purity [Giovannini, R. and Freitag, R., Biotechnol. Bioeng., 73:522-529 (2001); Schubert, S. and Freitag, R., J. Chromatogr., A. 1142:106-113 (2007)] and aggregate removal [Gagnon, P., BioProcess Int., 4(2):50-60 (2006); Guerrier, L. et al., Journal of Chromatography, B: 755:37-46 (2001)]. In more recent years, a variety of other additives, such as polyethylene glycol (PEG) [Gagnon, P. J. Immunol. Meth., 336: 222-228 (2008)], have been employed as elution modifiers. PEG has been shown to improve aggregate separation by differentially enhancing retention of larger solutes [Gagnon, P. J. Immunol. Meth., 336:222-228 (2008)]. The size of MVM particles is approximately 18-26 nm [Crawford, L V. Virology, 29:605-612 (1966)] while that of X-MuLV is 80-110 nm.

A study performed several years ago [Ng, P. et al., "Monoclonal Antibody Purification with CHT", Genetic Engineering News, August 2006, Vol. 26, No. 14, p. 60; Gagnon, P. et al., Bio-Rad Laboratories Technical Note, 2156 (2002); Gagnon, P. et al., "The practical task of purifying antibodies with ceramic hydroxyapatite", 11th Annual Waterside Conference, May 1-3, Chicago (2006)] demonstrated >3 and 2 log clearance of X-MuLV and MVM, respectively, in a sodium chloride gradient. The current study expands on these data and confirms that PEG provides additional clearance X-MuLV and MVM at an antibody loading level consistent with current manufacturing processes.

Materials and Methods

Antibody and Viral Solutions

A monoclonal antibody, purified over a protein A column, was generously supplied by Avid Bioservices (Tustin, Calif., USA). The eluate was neutralized to pH 7.0 and 0.5 M sodium phosphate, pH 7.0 was added to a final concentration of 10 mM. Antibody was loaded onto CHT columns at ~10 mg protein/mL bed volume.

Stock solutions of either minute virus of mice (MVM) or xenotropic murine leukemia virus (x-MuLV) (Charles River Laboratories, Malvern, Pa., USA) were used for this study. CHT:

Ceramic hydroxyapatite (CHT™), type I, 40 micron, was supplied by Bio-Rad Laboratories (Hercules, Calif., USA). The CHT was packed in 11.8×100 mm columns (Atoll GmbH, Weingarten, Germany). For all steps, the linear flow rate was 300 cm/hr. All runs were performed at room temperature.

Chromatography Buffers:

The following buffers were employed for this study. Each buffer was tested for cytotoxicity and interference in the infectivity assay systems used to quantitate each virus.
A) 10 mM sodium phosphate, pH 7.0
B) 10 mM sodium phosphate, 10% PEG-1000 (Sigma-Aldrich, St. Louis, Mo., USA), pH 7.0
C) 10 mM sodium phosphate, 2 M NaCl, pH 7.0
D) 30 mM sodium phosphate, 2 M NaCl, 10% PEG-1000, pH 7.0
E) 600 mM potassium phosphate, pH 7.0

Running Conditions:

I. NaCl Elution

The column was equilibrated with Buffer A. Following sample application the column was washed with 10 column volumes (CV) of Buffer A and eluted with a 10 column volume gradient to Buffer C. The gradient was held at 100% Buffer C until the antibody peak returned to baseline. The column was then cleaned with Buffer E and sanitized with 1 M NaOH. Each experiment was run in duplicate.

II. PEG/NaCl Elution

The CHT column was equilibrated with buffer A.

Equilibration and sample application were as described in the NaCl elution above. The column was then washed with 10 CV of Buffer A and 5 CV of Buffer B. Elution was a 10 column volume gradient to Buffer D. The gradient was held at 100% Buffer D until the antibody peak returned to baseline. The column was then cleaned with Buffer E and sanitized with 1 M NaOH. Each experiment was run in duplicate.

Viral Testing

Aliquots of antibody were mixed in a 1:20 ratio with virus stock solutions. A process control sample was removed and divided into two aliquots (spiked load and hold control). The spiked load was tested immediately; the hold control was kept at room temperature throughout the chromatography and then tested. Virus was also diluted into a media control and either assayed immediately or at the end of the chromatography (media control immediate and end samples, respectively). The rest of the aliquot was divided into two parts and chromatographed in duplicate. The flow-through+wash, eluate and column strip fractions were collected during each run and tested immediately via infectivity assay. The amount of virus present in each sample was determined by dilution techniques and the log clearance for each sample calculated from these data.

In some cases, samples were frozen and subsequently assayed for viral DNA via quantitative polymerase chain reaction. Each sample or control was amplified in triplicate for each dilution. Controls included cellular RNA and water for preparation of viral cDNA and negative control DNA and XuLV cDNA for amplification controls, as well as system suitability controls using β-actin. Amplification was performed using an Applied Biosystems Prism 7700 Sequence Detection System (Life Technologies, Carlsbad, Calif., USA). The number of viral equivalents measured from these assays were then determined and log clearance values derived from these data.

Results and Conclusions

The infectivity assay results of the X-MuLV and MVM clearance experiments are shown in Tables 1 and 2, respectively. Quantitative PCR data are shown in Table 3 and a summary of all data is presented in Table 4.

TABLE 1

Clearance of X-MuLV on CHT

| | NaCl | | PEG/NaCl | |
|---|---|---|---|---|
| Sample | Total Virus ($\log_{10}$) | Clearance ($\log_{10}$) | Total Virus ($\log_{10}$) | Clearance ($\log_{10}$) |
| Media Control Immediate | 7.28 | — | 6.93 | — |
| Spiked Load Run 1 | 7.07 | — | 7.19 | — |
| Flowthrough Run 1 | 3.57 | 3.50 | 3.94 | 3.25 |
| Eluate Run 1 | 3.89 | 3.18 | <3.15 | >4.04 |
| Column Strip Run 1 | 6.20 | 0.87 | 6.16 | 1.03 |
| Hold Control Run 1 | 7.27 | −0.20 | 7.25 | −0.06 |
| Spiked Load Run 2 | 7.06 | — | 7.19 | — |
| Flowthrough Run 2 | 3.67 | 3.39 | 3.89 | 3.30 |
| Eluate Run 2 | 3.39 | 3.67 | <3.08 | >4.11 |
| Column Strip Run 2 | 6.31 | 0.75 | 5.87 | 1.32 |
| Hold Control Run 2 | 7.27 | −0.21 | 7.25 | −0.06 |
| Media Control End | 7.11 | 0.17 | 7.00 | −0.07 |

TABLE 2

Clearance of MVM on CHT

| | NaCl | | PEG/NaCl | |
|---|---|---|---|---|
| Sample | Total Virus ($\log_{10}$) | Clearance ($\log_{10}$) | Total Virus ($\log_{10}$) | Clearance ($\log_{10}$) |
| Media Control Immediate | 8.95 | — | 8.81 | — |
| Spiked Load Run 1 | 9.28 | — | 9.15 | — |
| Flowthrough Run 1 | 8.55 | 0.73 | 8.69 | 0.46 |
| Eluate Run 1 | 7.49 | 1.79 | 6.60 | 2.55 |
| Column Strip Run 1 | 8.83 | 0.45 | 8.67 | 0.48 |
| Hold Control Run 1 | 9.16 | 0.12 | 9.08 | 0.07 |
| Spiked Load Run 2 | 9.28 | — | 9.15 | — |
| Flowthrough Run 2 | 8.57 | 0.71 | 8.36 | 0.79 |
| Eluate Run 2 | 7.68 | 1.60 | 6.39 | 2.76 |
| Column Strip Run 2 | 8.87 | 0.41 | 8.76 | 0.39 |
| Hold Control Run 2 | 9.16 | 0.12 | 9.08 | 0.07 |
| Media Control End | 8.90 | 0.05 | 8.70 | 0.11 |

TABLE 3

Quantitative PCR on X-MuLV clearance using NaCl + PEG

| Sample | Total Virus ($\log_{10}$) | Clearance ($\log_{10}$) |
|---|---|---|
| Spiked Load | 10.67 | — |
| Hold Control | 10.72 | −0.05 |
| Eluate Run 1 | 6.66 | 4.01 |
| Eluate Run 2 | 6.53 | 4.15 |

TABLE 4

Summary of viral clearance data (load to eluate)

| | X-MuLV Clearance ($\log_{10}$) | | | MVM Clearance ($\log_{10}$) | | |
|---|---|---|---|---|---|---|
| Condition | Run 1 | Run 2 | Average | Run 1 | Run 2 | Average |
| NaCl | 3.18 | 3.67 | 3.43 | 1.79 | 1.60 | 1.70 |
| PEG/NaCl | >4.04 | >4.11 | >4.08 | 2.55 | 2.76 | 2.66 |
| PEG/NaCl (qPCR) | 4.01 | 4.15 | 4.08 | N/A | N/A | |

TABLE 4-continued

Summary of viral clearance data (load to eluate)

| | X-MuLV Clearance (Log$_{10}$) | | | MVM Clearance (Log$_{10}$) | | |
|---|---|---|---|---|---|---|
| Condition | Run 1 | Run 2 | Average | Run 1 | Run 2 | Average |

N/A, not assayed

The tight binding of viruses to CHT can be explained at least in part by the multi-modal nature of hydroxyapatite interactions. For enveloped viruses, the significant number of phosphate groups on the lipid envelope interact strongly with the calcium atoms via a chelation mechanism as has been previously shown for both proteins and nucleic acids [Sleigh, R W et al., *J Dairy Res.*, 46:337-42 (1979); Gagnon, P., *BioProcess Int.*, 4(2):50-60 (2006)]. In general, the much larger surface area provided by viruses would be expected to result in significantly tighter binding as compared to much smaller bio-molecules (such as antibodies). Such an effect has been noted for IgG antibody aggregates, which generally elute later on hydroxyapatite in a gradient than monomeric IgG, and for larger antibody types such as IgA and IgM [Aoyama, K. and Chiba, J., *J Imm. Meth.*, 162:201-210 (1993); Luellau, E. et al., *Journal of Chromatography*, A, 796:165-175 (1998); Josic D. et al., *Biol. Chem. Hoppe Seylar*, 372(3):149-156 (1991), Gagnon, P. *J. Immunol. Meth.*, 336:222-228 (2008)]. The effect is similar to that observed on cation exchange resins (see, for example, 19).

The data from Tables 1 and 2 indicate, first, that the experimental conditions in and of themselves did not inactivate either virus, nor were the viruses themselves inherently unstable since all hold controls had the same virus titers to within 0.5 log as the initial measurements. In addition, approximately 80% or greater of the applied viruses in the loads were recovered in the fractions analyzed, indicating good mass balance for these studies. It should be noted that the majority of both viruses appear in the column strip fractions.

The X-MuLV clearance in NaCl alone confirms the previously-reported value of >3 logs [Gagnon, P. et al., "The practical task of purifying antibodies with ceramic hydroxyapatite", 11th Annual Waterside Conference, May 1-3, Chicago (2006)] for this type of gradient elution. Clearance was increased by 0.6 log when PEG at a fixed concentration was added to the NaCl gradient. Similar confirmation of existing data with MVM clearance [Gagnon, P. et al., "The practical task of purifying antibodies with ceramic hydroxyapatite", 11th Annual Waterside Conference, May 1-3, Chicago (2006)] in NaCl gradients was also obtained. Here, the use of PEG in combination with NaCl removed greater than 10 times more virus. This capability enables potentially significant improvements in product safety.

The effect of PEG may reflect its previously-documented ability to cause tighter binding of aggregates compared to monomers to a variety of chromatographic supports [Luellau, E. et al., *Journal of Chromatography*, A, 796:165-175 (1998); Gagnon, P. et al., *Chromatogr., A* 743:51-55 (1996)]. Because the number of plaques for the PEG/NaCl eluates fell below the quantitation level for X-MuLV, only minimum clearance values could be reported. To address this, quantitative PCR was performed on these samples; the data reveal that just over 4 logs clearance was obtained, in agreement with the plaque assay system.

These data indicate that CHT reliably removes X-MuLV up to 4 logs, and can remove MVM in the range of 1-2 logs. The vast majority of the recovered X-MuLV is recovered in the regeneration fraction, which is obtained by stripping the column with a benign (neutral phosphate) buffer.

It will be understood by the person of ordinary skill in the art how to scale up the results from experiments such as those described in the above examples, to whatever volume required to meet their particular requirements. It will also be understood by such persons that other approaches to method development, such as high-throughput robotic approaches, can be applied to determine the conditions that most effectively embody the invention for a particular antibody.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method for enhancing protein binding capacity of a mixed mode chromatography support, the method comprising
    contacting said support with a protein preparation in the presence of an aqueous-soluble nonionic organic polymer; and
    eluting a target protein from the support in the presence of the aqueous-soluble nonionic organic polymer, wherein
        (a) the preparation comprises antibodies, and a non-antibody target protein that is substantially free from antibodies is collected and the non-antibody target protein is submitted to at least one further purification step; or
        (b) the preparation does not comprise antibodies.

2. The method of claim 1, wherein the preparation comprises antibodies and a non-antibody target protein that is substantially free from antibodies is collected and the target protein is submitted to at least one further purification step.

3. The method of claim 1, wherein the preparation does not comprise antibodies.

4. The method of claim 1, wherein the nonionic organic polymer is from the group consisting of dextran, starch, cellulose, polyvinylpyrrolidone, polypropylene glycol and polyethylene glycol (PEG).

5. The method of claim 1, wherein the nonionic organic polymer comprises two or more nonionic inorganic polymers.

6. The method of claim 1, wherein the nonionic organic polymer has an average molecular weight of 100 to 10,000 daltons.

7. The method of claim 1, wherein the mixed mode support exploits a combination of two or more of the following functionalities to adsorb components of the preparation: cation exchange, anion exchange, hydrophobic interaction, hydrophilic interaction, hydrogen bonding, pi-pi bonding, metal affinity.

8. The method of claim 1, wherein the mixed mode support comprises hydroxyapatite.

9. The method of claim 8, wherein the mixed mode support is selected from the group consisting of hydroxyapatite CHT Type I, 20 micron; hydroxyapatite CHT Type I, 40 micron; hydroxyapatite CHT Type I, 80 micron; hydroxyapatite CHT Type II, 20 micron; hydroxyapatite CHT Type II, 40 micron; and hydroxyapatite CHT Type II, 80 micron.

10. The method of claim 1, wherein the mixed mode support comprises fluoroapatite.

11. The method of claim 10, wherein the mixed mode support comprises fluoroapatite CFT Type I, 40 micron or fluoroapatite CFT Type II, 40 micron.

12. The method of claim 1, wherein the mixed mode support comprises a ligand selected from the group consisting of Capto-MMC, Capto-Adhere, Capto-S, Capto-Q, MEP Hypercel, and ABx.

13. The method of claim 1, wherein the method comprises at least one other purification step.

14. The method of claim 1, wherein separation of virus from the target protein on the mixed mode chromatography support operated in bind elute mode is enhanced compared to the separation that would occur in the absence of the aqueous-soluble nonionic organic polymer.

15. The method of claim 1, wherein retention on the support of aggregates, virus, and other contaminants larger than the target protein is enhanced to a greater degree than retention of the target protein, and wherein separation of the aggregates, virus, and other contaminants from the target protein is thereby increased.

16. The method of claim 1, wherein retention on the support of aggregates, virus, and other contaminants larger than the target protein is enhanced to a greater degree than retention of the target protein and wherein the method allows for increased capacity for contaminant removal from the target protein.

17. The method of claim 1, wherein retention on the support of the target protein is enhanced to a greater degree than retention of molecules smaller than the target protein, and wherein separation of the molecules from the target protein is thereby increased.

* * * * *